United States Patent [19]

Millauer

[11] Patent Number: 5,599,989
[45] Date of Patent: Feb. 4, 1997

[54] BISQUATERNARY AMMONIUM COMPOUNDS OF 2,2'-DIMETHYL-1,1'-BINAPHYTHYL AND PROCESS FOR THEIR PREPARATION

[75] Inventor: Hans Millauer, Eschborn, Germany

[73] Assignee: Hoechst Aktiengesellschaft, Frankfurt, Germany

[21] Appl. No.: 449,677

[22] Filed: May 24, 1995

[30] Foreign Application Priority Data

May 26, 1994 [DE] Germany ............ 44 18 349.6

[51] Int. Cl.$^6$ ............ C07C 211/63; C07C 209/12; C07C 209/22
[52] U.S. Cl. ............ 564/290; 540/460; 544/357; 544/162; 546/191
[58] Field of Search ............ 564/290; 546/191; 544/357, 162; 540/460

[56] References Cited

U.S. PATENT DOCUMENTS 2,744,902  5/1956  Harris ............ 260/290

FOREIGN PATENT DOCUMENTS 0630884  12/1994  European Pat. Off. .

OTHER PUBLICATIONS

Maigrot et al. Chem Abst. 103:215265 (1986).

*Primary Examiner*—Peter O'Sullivan
*Attorney, Agent, or Firm*—Connolly and Hutz

[57] ABSTRACT

The invention relates to bisquaternary ammonium compounds of the formula (I)

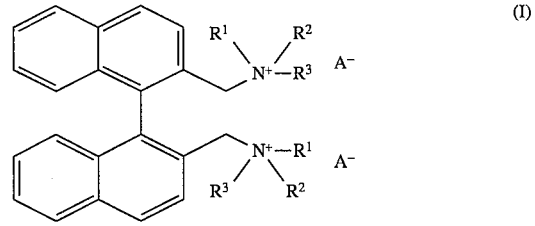

and their preparation, where:

$R^1$, $R^2$, $R^3$ are, for example, identical or different ($C_1$–$C_{12}$)alkyl which can also contain oxygen atoms or N—$R^4$ moieties, where $R^4$ is ($C_1$–$C_4$)alkyl, in the chain and A is a chlorine, bromine, iodine atom or a $OSO_3R^5$ radical, where $R^5$ is ($C_1$–$C_4$) alkyl or aryl.

23 Claims, No Drawings

BISQUATERNARY AMMONIUM COMPOUNDS OF 2,2'-DIMETHYL-1,1'-BINAPHYTHYL AND PROCESS FOR THEIR PREPARATION

DESCRIPTION

The invention relates to bisquaternaryammonium compounds of 2,2'-dimethyl-1,1'-binaphthyl and processes for their preparation.

Bisquaternary ammonium compounds of 2,2'-dimethyl-1, 1'-binaphthyl are important intermediates for the preparation of bistertiary phosphines.

Phosphines having two tertiary phosphine groups in the molecule, which groups bear bulky aromatic or araliphatic radicals, are used as bidentate ligands for complexing heavy metal atoms such as palladium or rhodium. In particular, bidentate ligands which are structurally derived from 1,1'-binaphthyl and bear (diphenylphosphino)methyl groups as substituents in the 2 and 2' positions known under the term "Naphos", form very stable complexes which are used as catalysts in a series of important industrial processes, e.g. hydrogenations and oxo syntheses.

The German Patent Application P 44 18 346.1, filed on the same day, describes a very advantageous process for preparing tertiary phosphines for which the ammonium compounds of the invention are required as starting materials.

It is thus an object of the invention to provide such compounds.

This object is achieved by compounds of the formula (I)

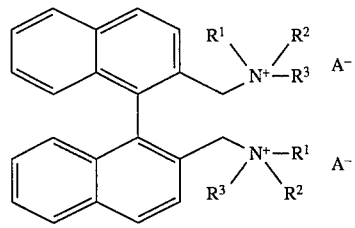

(I)

where:

- $R^1, R^2, R^3$ are identical or different and are $(C_1-C_{12})$-alkyl which can also contain oxygen atoms or $N-R^4$ moieties, where $R^4$ is $(C_1-C_4)$alkyl, in the chain or
- $R^1$ is $(C_4-C_8)$ cycloalkyl and $R^2$, $R^3$ are identical or different and are $(C_1-C_{12})$alkyl or
- the two radicals $R^1$ together form an alkylene chain having from 2 to 6 carbon atoms and $R^2$, $R^3$ are identical or different and are $(C_1-C_{12})$alkyl or
- the radicals $R^1$ and $R^2$ located on the same nitrogen atom together form a 5-membered or 6-membered ring, which can also contain oxygen atoms or $N-R^4$ moieties, where $R^4$ is $(C_1-C_4)$alkyl, in the chain and the radical $R^3$ is an alkyl radical having from 1 to 12 carbon atoms or
- the radicals $R^1, R^2, R^3$ located on the same nitrogen atom together form a bicyclic ring system having a nitrogen atom as bridge head atom and, if desired, further oxygen atoms or $N-R^4$ moieties, where $R^4$ is $(C_1-C_4)$alkyl, in the ring system and
- A is a chlorine, bromine, iodine atom or a $OSO_3R^5$ radical, where $R^5$ is $(C_1-C_4)$alkyl or aryl.

Of great interest are, for example, the following compounds of the formula (I):

2,2'-bis [(trimethylammonio) methyl]-1,1'-binaphthyl salts 2,2'-bis[(triethylammonio)methyl]-1,1'-binaphthyl salts
2,2'-bis[(tripropylammonio)methyl]-1,1'-binaphthyl salts
2,2'-bis[(tributylammonio)methyl]-1,1'-binaphthyl salts
2,2'-bis[(trihexylammonio)methyl]-1,1'-binaphthyl salts
2,2'-bis[(trioctylammonio)methyl]-1,1'-binaphthyl salts
2,2'-bis[(N-ethyldimethylammonio)methyl]-1,1'-binaphthyl salts
2,2'-bis[(N,N-dimethylbutylammonio)methyl]-1, 1'-binaphthyl salts
2,2'-bis[(N,N-dimethylcyclohexylammonio)methyl]-1,1'-binaphthyl salts
2,2'-bis[(N,N-dicyclohexylmethylammonio)methyl]-1,1'-binaphthyl salts
2,2'-bis[(N-methylpiperidinio)methyl]-1,1'-binaphthyl salts
2,2'-bis[(N,N'-dimethylpiperazinio)methyl]-1,1'-binaphthyl salts
2,2'-bis[(N-methylmorpholinio)methyl]-1,1'-binaphthyl salts.

Of particular importance are also:

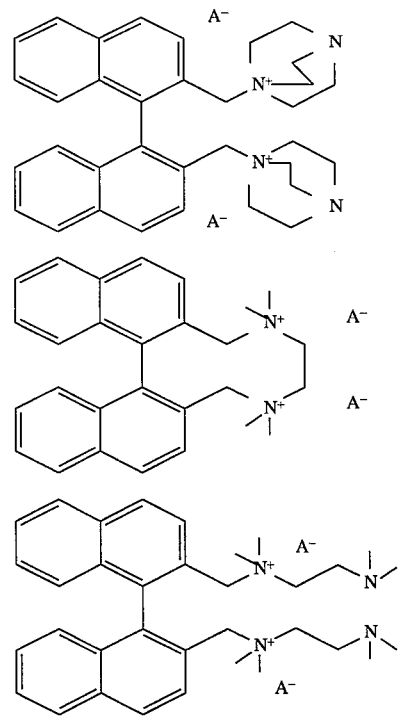

The invention further provides a process for preparing the compounds of the formula (I), which comprises reacting compounds of the formula (II)

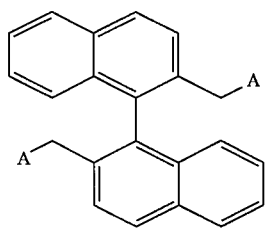

(II)

where A is as defined above, at temperatures of from 20° to 150° C. in the presence of a solvent, at atmospheric or superatmospheric pressure, with a nitrogen base of the formula (III)

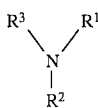

where $R^1$, $R^2$ and $R^3$ are as defined above.

Since the products of the invention having the formula (I) in many cases tend to form stable solvate complexes with the solvent used, care should be taken in selecting the solvent that this does not interfere in the subsequent reaction step. Suitable solvents are, for example, hydrocarbons, ethers, halogenated hydrocarbons, ketones, nitro compounds or nitriles.

Solvents which have been found to be suitable in many cases are, for example: isohexane, n-heptane, cyclohexane, hydrocarbon fractions (petroleum spirit) having boiling point ranges between 70° and 250° C., toluene, xylene, methyl t-butyl ether, diisopropyl ether, tetrahydrofuran, chloroform, chlorobenzene, acetone, methyl i-butyl ketone, nitromethane, acetonitrile, dimethylformamide and dimethylacetamide; preference is given to chlorobenzene and dimethylformamide.

The reaction temperatures are preferably from 50 to 120° C. When using readily volatile amines, the use of increased pressure is useful. The pressure range required is between 1 and about 10 bar. The reaction time is between 1 and 12 hours.

The reaction mixture is advantageously stirred continuously during the reaction. The products of the invention having the formula (I) are sparingly soluble in some of the solvents used and precipitate during the reaction. In this case, the products are separated off by filtration. If the process products are soluble, they can be isolated by distilling off the solvent and, if appropriate, the excess amine.

When using certain solvents such as, for example, dimethylformamide, dimethylacetamide, acetonitrile or tetrahydrofuran the isolation of the product can be omitted; in this case the reaction mixture can be used directly in the subsequent reaction step.

The starting compounds of the formula (II) which are required for preparing the products of the invention having the formula (I) can be obtained, for example, by side-chain bromination of 2,2'-dimethyl-1,1'-binaphthyl using known methods. The tertiary amines required as starting compounds of the formula (III) are known and most are commercially available, they are prepared by known methods.

EXAMPLE 1

A stirred flask having a capacity of 100 ml and fitted with a reflux condenser which can be cooled to −20° C., thermometer and heating bath is charged with 11.0 g (0.025 mol) of 2,2'-bis(bromomethyl)-1,1'-binaphthyl, 4.43 g (0.075 mol) of trimethylamine in 50 ml of dimethylformamide and the mixture is gradually heated to 70° C. while stirring. Stirring is continued for 3 hours at this temperature. After cooling to room temperature, the precipitated product is filtered off with suction, washed with a little cold dimethylformamide and dried in a vacuum desiccator over concentrated sulfuric acid. The yield is 11.8 g (74% of theory) of 2,2'-bis[(trimethylammonio)methyl]-1,1'-binaphthyl dibromide; after drying, the product still contains one molecule of dimethylformamide.

$^1$H-NMR (300 MHz, $D_2O$) δ in ppm, $D_2O$ as reference:
7.2–8.2 (12H, aryl-H)
4.7 (2H, aryl-C$\underline{H}^A H^B$—$N^+$)
3.9 (2H, aryl-C$\underline{H}^A H^B$—$N^+$, $J_{AB}$=15 Hz)
2.6 (18H, —$N^+$ (C$\underline{H}_3$)$_3$)

I claim:

1. A bisquaternary ammonium compound of the formula (I)

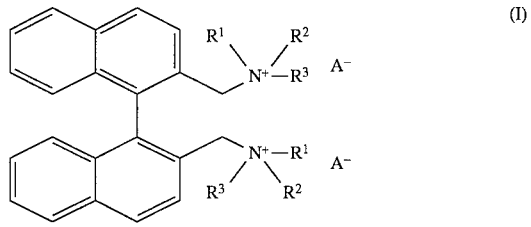

where:

$R^1$, $R^2$, $R^3$ are identical or different and are ($C_1$–$C_{12}$)alkyl which alkyl optionally contain oxygen atoms or N—$R^4$ moieties, where $R^4$ is ($C_1$–$C_4$)alkyl, in the chain or $R^1$ is ($C_4$–$C_8$)cycloalkyl and $R^2$, $R^3$ are identical or different and are ($C_1$–$C_{12}$)alkyl or the two radicals $R^1$ together form an alkylene chain having from 2 to 6 carbon atoms and $R^2$, $R^3$ are identical or different and are ($C_1$–$C_{12}$)alkyl or the radicals $R^1$ and $R^2$ located on the same nitrogen atom together form a 5-membered or 6-membered ring, which ring optionally contains oxygen atoms or N—$R^4$ moieties, where $R^4$ is ($C_1$–$C_4$)alkyl, in the chain and the radical $R^3$ is an alkyl radical having from 1 to 12 carbon atoms or the radicals $R^1$, $R^2$, $R^3$ located on the same nitrogen atom together form a bicyclic ring system having a nitrogen atom as bridge head atom and, optionally, further oxygen atoms or N—$R^4$ moieties, where $R^4$ is ($C_1$–$C_4$)alkyl, in the ring system and A is a chlorine, bromine, iodine atom or a $OSO_3R^5$ radical, where $R^5$ is ($C_1$–$C_4$)alkyl or aryl.

2. A compound according to claim 1 of the formula (I) from the group consisting of:

2,2'-bis[(trimethylammonio)methyl]-1,1'-binaphthyl salts 2,2'-bis[(triethylammonio)methyl]-1,1'-binaphthyl salts 2,2'-bis[(tripropylammonio)methyl]-1,1'-binaphthyl salts 2,2'-bis[(tributylammonio)methyl]-1,1'-binaphthyl salts 2,2'-bis[(trihexylammonio)methyl]-1,1'-binaphthyl salts 2,2'-bis[(trioctylammonio)methyl]-1,1'-binaphthyl salts 2,2'-bis[(N-ethyldimethylammonio)methyl]-1,1'-binaphthyl salts 2,2'-bis[(N,N-dimethylbutylammonio)methyl]-1,1'-binaphthyl salts 2,2'-bis[(N,N-dimethylcyclohexylammonio)methyl]-1,1'-binaphthyl salts 2,2'-bis[(N,N-dicyclohexylmethylammonio)methyl]-1,1'-binaphthyl salts 2,2'-bis[(N-methylpiperidinio)methyl]-1,1'-binaphthyl salts 2,2'-bis[(N,N'-dimethylpiperazinio)methyl]-1,1'-binaphthyl salts and 2,2'-bis[(N-methylmorpholinio)methyl]-1,1'-binaphthyl salts.

3. A compound according to claim 1 of the formula (I) from the group consisting of:

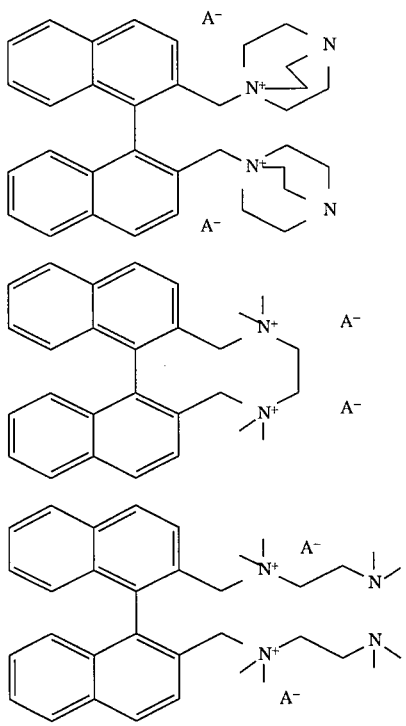

4. A process for preparing the compounds according to claim 1 of the formula (I), which comprises reacting compounds of the formula (II)

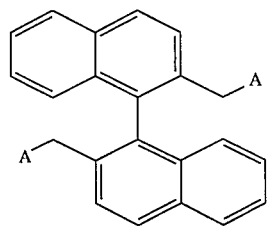

where A is as defined above, at temperatures of from 20° to 150° C. in the presence of a solvent, at atmospheric or superatmospheric pressure, with a nitrogen base of the formula (III)

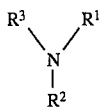

where $R^1$, $R^2$ and $R^3$ are as defined in claim 1.

5. The process as claimed in claim 4, wherein hydrocarbons, ethers, halogenated hydrocarbons, ketones, nitro compounds or nitriles are used as solvent.

6. The process as claimed in claim 4, wherein isohexane, n-heptane, cyclohexane, hydrocarbon fractions (petroleum spirit) having boiling point ranges between 70° and 250° C., toluene, xylene, methyl t-butyl ether, diisopropyl ether, tetrahydrofuran, chloroform, chlorobenzene, acetone, methyl i-butyl ketone, nitromethane, acetonitrile, dimethylformamide or dimethylacetamide are used as solvent.

7. The process as claimed in claim 4, wherein chlorobenzene or dimethylformamide are used as solvent.

8. The process as claimed in claim 4, wherein the reaction is carried out at temperatures of from 50° to 120° C.

9. The process as claimed in claim 4, wherein the reaction is carried out at a pressure of from 1 to 10 bar.

10. A bisquaternary ammonium compound of the formula

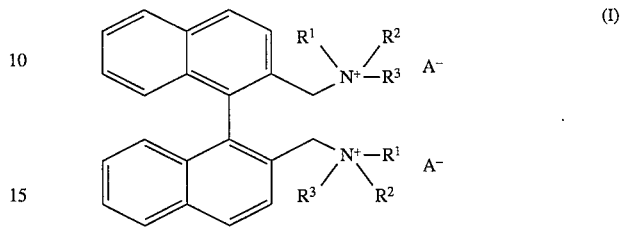

wherein $R^1$, $R^2$, $R^3$ are identical or different and are $(C_1-C_{12})$ alkyl, which alkyl optionally contain oxygen atoms or N—$R^4$ moieties, where $R^4$ is $(C_1-C_4)$ alkyl, in the chain and A is a chlorine, bromine, iodine atom or a $OSO_3R^5$ radical, wherein $R^5$ is $(C_1-C_4)$ alkyl or aryl.

11. A bisquaternary compound according to claim 1, consisting of salts of 2,2'-bis[(trimethylammonio)methyl]-1,1'-binaphthyl.

12. A bisquaternary compound according to claim 1, consisting of salts of 2,2'-bis[(triethylammonio)methyl]-1,1'-binaphthyl.

13. A bisquaternary compound according to claim 1, consisting of salts of 2,2'-bis[(tripropylammonio)methyl]-1,1'-binaphthyl.

14. A bisquaternary compound according to claim 1, consisting of salts of 2,2'-bis[(tributylammonio)methyl]-1,1'-binaphthyl.

15. A bisquaternary compound according to claim 1, consisting of salts of 2,2'-bis[(trihexylammonio)methyl]-1,1'-binaphthyl.

16. A bisquaternary compound according to claim 1, consisting of salts of 2,2'-bis[(trioctylammonio)methyl]-1,1'-binaphthyl.

17. A bisquaternary compound according to claim 1, consisting of salts of 2,2'-bis[(N-ethyldimethylammonio)methyl]-1,1'-binaphthyl.

18. A bisquaternary compound according to claim 1, consisting of salts of 2,2'-bis[(N,N-dimethylbutylammonio)methyl]-1,1'-binaphthyl.

19. A bisquaternary compound according to claim 1, consisting of salts of 2,2'-bis[(N,N-dimethylcyclohexylammonio)methyl]-1,1'-binaphthyl.

20. A bisquaternary compound according to claim 1, consisting of salts of 2,2'-bis[(N,N-dicyclohexylmethylammonio)methyl]-1,1'-binaphthyl.

21. A bisquaternary compound according to claim 1, consisting of salts of 2,2'-bis[(N-methylpiperidinio)methyl]-1,1'-binaphthyl.

22. A bisquaternary compound according to claim 1, consisting of salts of 2,2'-bis[(N,N'-dimethylpiperazinio)methyl]-1,1'-binaphthyl.

23. A bisquaternary compound according to claim 1, consisting of salts of 2,2'-bis[(N-methylmorpholinio)methyl]-1,1'-binaphthyl.

* * * * *